US009580761B2

(12) United States Patent
Roth

(10) Patent No.: US 9,580,761 B2
(45) Date of Patent: Feb. 28, 2017

(54) EXOGENOUS INTERNAL POSITIVE CONTROL

(75) Inventor: Bernhard Roth, Marburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/001,462

(22) PCT Filed: Feb. 24, 2012

(86) PCT No.: PCT/IB2012/050859
§ 371 (c)(1),
(2), (4) Date: Oct. 16, 2013

(87) PCT Pub. No.: WO2012/114312
PCT Pub. Date: Aug. 30, 2012

(65) Prior Publication Data
US 2014/0370494 A1 Dec. 18, 2014

Related U.S. Application Data

(60) Provisional application No. 61/463,980, filed on Feb. 25, 2011.

(51) Int. Cl.
*C12Q 1/70* (2006.01)
*G01N 33/569* (2006.01)

(52) U.S. Cl.
CPC ....... *C12Q 1/701* (2013.01); *G01N 33/56983* (2013.01); *C12N 2720/12251* (2013.01); *C12N 2760/16151* (2013.01); *C12N 2760/16251* (2013.01); *C12N 2770/40031* (2013.01); *G01N 2333/11* (2013.01)

(58) Field of Classification Search
None
See application file for complete search history.

(56) References Cited

U.S. PATENT DOCUMENTS

| 6,077,661 | A | 6/2000 | Natarajan et al. |
| 7,250,496 | B2 | 7/2007 | Bentwich et al. |
| 7,696,334 | B1 | 4/2010 | Bentwich et al. |
| 7,940,387 | B2 | 5/2011 | Dluhy et al. |
| 2009/0081252 | A1* | 3/2009 | Gregersen .................. 424/206.1 |
| 2011/0225683 | A1 | 9/2011 | Dietrich et al. |

FOREIGN PATENT DOCUMENTS

| JP | 3560974 B2 | 9/2004 | |
| JP | 3594598 B2 | 12/2004 | |
| JP | 2009-513694 A | 4/2009 | |
| WO | WO-94/04706 A1 | 3/1994 | |
| WO | WO-95/02067 A1 | 1/1995 | |
| WO | WO-01/46463 A2 | 6/2001 | |
| WO | WO-03/084384 A2 | 10/2003 | |
| WO | WO 2007/052163 | * 5/2007 | ............ A61K 39/00 |
| WO | WO-2007/052163 A2 | 5/2007 | |
| WO | WO-2008/068631 A2 | 6/2008 | |
| WO | WO-2008/145196 A1 | 12/2008 | |
| WO | WO-2010/031918 A1 | 3/2010 | |

OTHER PUBLICATIONS

Wagter et al (Veterinary Research Communications 20:401-408, 1996).*
Dreier et al (Journal of Clinical Microbiology 43:4551-4557, 2005).*
Chidlow et al (Viruses 1:42-56, 2009).*
Dreier et al. Use of Bacteriophage MS2 as an Internal Control in Viral Reverse Transcription-PCR Assays. J. Clin. Microbiol. 2005; 43:4551-4557.*
Chidlow et al. An Economical Tandem Multiplex Real-Time PCR Technique for the Detection of a Comprehensive Range of Respiratory Pathogens. Viruses. 2009; 1:42-56.*
Fortin et al. Additions and Corrections: Hyper-responsiveness to stimulation of human immunodeficiency virus-infected CD4_ T cells requires Nef and Tat virus gene products and results from higher NFAT, NF-_B, and AP-1 induction. J. Biol. Chem. 2005; 280(10): 2752.*
Welsch et al. Electron Tomography Reveals the Steps in Filovirus Budding. PLoS-Pathogens, 6(4): e1000875. doi:10.1371/journal.ppat.1000875: pp. 1-9.*
ATCCProductSheet_PVMC-61.pdf.*
Mairhofer et al. Use of Tomato Mosaic Virus (ToMV) as Internal Positive Control (IPC) in different RT-PCR settings. HN 2007. http://www.gene-quantification.com/qpcr2007/Nitschko-qPCR-2007.pdf; pp. 1-13; downloaded May 24, 2016.*
Welsch et al. Electron Tomography Reveals the Steps in Filovirus Budding. PLoS-Pathogens, 2010; 6(4): e1000875. doi:10.1371/journal.ppat.1000875: pp. 1-9.*
Martelli et al. The family *Tymoviridae*. Arch. Virol. 2002; 147(9): 1837-1846.*
ATCCProductSheet_PVMC-61.pdf 2013.*
Zhai et al. Isolation of Protoplasts from Tissues of 14-day-old Seedlings of Arabidopsis thaliana. J. Vis. Exp. 2009; 30: 1-3 (DOI: 10.3791/1149).*
Mairhofer et al. (2007). "Use of tomato mosaic virus (ToMV) as internal positive control (IPC) in different RT-PCR settings," Retrieved Jul. 30, 2012 from http://www.gene-quantification.de/gpcr2007/Nitschko-qPCR-2007.pdf.
International Search Report, mailed on Aug. 22, 2012, for PCT Application No. PCT/IB2012/050859, filed on Feb. 24, 2012, 8 pages.
Written Opinion of the International Searching Authority, mailed on Aug. 22, 2012, for PCT Application No. PCT/IB2012/050859, 9 pages.

(Continued)

*Primary Examiner* — Janet L Andres
*Assistant Examiner* — Stuart W Snyder
(74) *Attorney, Agent, or Firm* — Morrison & Foerster LLP

(57) ABSTRACT

The present invention provides an internal positive control for contaminating viruses. The invention provides the use of a second virus as an exogenous internal positive control in methods for verifying the reliability of an assay to detect a first virus, in methods of ensuring the absence of the first virus in a biological sample or pharmaceutical sample and in methods of manufacturing a vaccine free from a first virus.

11 Claims, No Drawings

(56) References Cited

OTHER PUBLICATIONS

Rodriguez-Sanchez et al. (2008). "Improved Diagnosis for Nine Viral Diseases Considered as Notifiable By the World Organization for Animal Health." Transbound. Emerg. Dis., 55:215-225.

* cited by examiner

SEQUENCE LISTING

```
<160> NUMBER OF SEQ ID NOS: 4

<210> SEQ ID NO 1
<211> LENGTH: 6304
<212> TYPE: DNA
<213> ORGANISM: Alliaria petiolata tymovirus

<400> SEQUENCE: 1
gattgaaggt ctggagaggt ggacggcttg aattcaagcc atagttttg atcctcttag      60 tgacaatcaa aaacggcccc atttaaccgc cccttgcaac cctcgtaaga catttgcaaa    120
tgagcaatgg ccttccaact tgccttggac gccttagccc cgaccacgca tcgggatcca    180
tctcttcacc ccatactcga atctaccgta gattcgatcc ggtcctcgat cactacctac    240
ccgtggtctg taccgaaaca acttctccct cttctcaact cttacggaat cccaacatct    300
ggtttgggaa cctcccacca cccccatgct gcccacaaga ccatcgagac atttctcctt    360
cacatccatt ggtctttcca ggccgtaact cccagttccg tgatgttcat gaagccaagc    420
aagtttcaca aactcgctcg cgtgaactcc aacttccgag aactgaagaa ctaccgactc    480
caaccaaccg acaccgttcg gtaccgtcc acctctccag accttccac tctcccgaca     540 gtgttcatgc acgacgccct gatgtattac catccgtcgc aaatcctaga cctcttcacc    600
caatgcccca ctctagagaa gctttacgca agtctagtgg tccctcccga agccaccctc    660
tccgaccact ctctttatcc cagcctctac acctacacca cctcccacca gacccttcat    720
tacgtgcccg aaggtcacga ggccggcagc tacaatcagc ccatcgacgc cctctcttgg    780
ctgaaagtga accagatctc tcacgccgac ctccacctca gcgtaaccat cttggaatct    840
tggggccccg tccactctct tcttatccaa cgtggactcc cgcaccagga cccagcgctc    900 ctgtcccct cagttccaac tcaatccgat ctgttcctct cctaccttca ccccgagaa      960 gacttggtgt ccttccggat tccagacgcc gtcctcctcc cagaagccac tttcttgaac   1020
caacctcttc gacaccgctt ggtccctcga gcagtgtaca actccctctt cacttacacc   1080
cgagccgtca gaacactcag gacgtcggac ccagcagcgt tcgtacgcat gcactcgtcc   1140
aaaccagagc acgactgggt cactccaacc gcctgggaca atctccaaac gttcgctctc   1200
ctaaacgtgc cccttcgtcc caacgtaatt taccaagtcc tccagagccc tttcgcctcc   1260
gcccgactgt acttgagtca acattggcga cgcctcgccc ccaccgccgc tcctatcctc   1320
tccttcctaa ccctccttca gcacttcctg ccgttgtctt tgcctctcgt caaggtaaag   1380
tccatctctc tctcttccgt caacggtatc acttccacag acctcctccg agaaagacac   1440
ggtggcccat ccctgagtca actcgccgac cacttcccgc acccgactc aatcgtccct     1500
```

```
tcatcggagt cagacaactg gagccaccca ttccttctca aggtcctcca gctgctccga    1560
cccatcgccc ccctcctgtc actaacacct ttctaccaag tcgagaaaat cccggtgcta    1620
cctcgcgctc aactttcttg gacccggaaa aacttcgctc tgccctggca ggcgtccctg    1680
ctcctactca caatctccga gctctccatc ttccttcaca aactcacctc ccctcccacc    1740
ctacaatctc agcacgatat ctaccatcgc cacatgcacc ctggatcatt caagctgatg    1800
tgggagagga aagctttgca agtctcgaga ctgactcctt ttcttccatt caatccctct    1860
acctccactc ccccccagga gttcttccag acggcgcacc acttcggacc ttcaattcag    1920
ccggaaccag tctttacgcc tcccacaatc ccccgagccc ctgctcttac gactacggca    1980
gcgccccaga caccgaagga agtccgacct ctcccatcaa ccaccgaagt cctccctatt    2040
cccactttcc cacaccagga cgtggtggcc cagctcaaca caggctccac ttggaccagt    2100
cagccccaac cccccccttg gtccactctc cttttcttcc cggaaacctc actccctccc    2160
caggtgtttc ccactgaacc gacgatttct tcgagcccccg attaccccctc caccgttcat    2220
caatcccgcg ctcccctctc cggctcccaa gctctcttgc ctcctcctct tccgtctgac    2280
aacaccgcca tcggccccgt gctgcaattt cagcagctct accccccgaag ttaccctgcc    2340
gacactgccg acttccacac ccgactccgc gccctccctc caactcctct tccccttccc    2400
cccctcaatt gccttctctc cgcagttctt cccaaaccaa cgtctccgag gaacatcttt    2460
ggcactctct ccaaaccatc ctcccagact ctaggtctct caacagacca cctcaccgcc    2520
atggcccacc tctacaattt ccaagccacg gtccactctg aacgcggccc tgtcaccttc    2580
ggcccctctg actctgtcaa acgaattcac ctctctcaca ctttcgggcc gccatctcac    2640
ttcacttctg ggccccgact ccttggcggc atgccgaatc caactcacct gaaccccaat    2700
ccacccttaa tccgagctct caaatccttc aaactcggag gtcactacct ccctttccaa    2760
cacgcacatc gtcacccctc ttcgatctcc cacgcgaaga atctgatttc aaacatgaaa    2820
aacgggttcg acgcgtcct ctccctcatt gacgtttcct ccaatcctcg gccgggtcac    2880
actccaaaag acaagatcat ccagctggac cggcaccttg acaccaaccc tgagaaaacc    2940
atctctgtgg tacatatcgc cggattcgct gggtgtggaa agaccccacc catccaaaaa    3000
ctccttttcca ccagactttt ccagaacttc cgagtctcca cccccaccac cgaacttcga    3060
aatgagtgga agacttccat gaacctgcct ggcaaccaat cctggcgatt ctgcacatgg    3120
gagtcctcct tgctgaaatc ttccaaaatc ctcgtgatcg acgaaatcta caaaatgcca    3180
agagggtacc ttgatctctc cattctcgct gatcctctcc ttgaactcgt catcatcctt    3240
gtcgacatcc atggatccga gtaccactca caatccaagg actcctccaa tcaccgcctg    3300
ccctcagaga ctggcaggct cgtacattac atcgacttct actgctggtg gagttaccgc    3360
atcccacaag ttatatctcg cctcttcaac atccacagct tcaacctgga ccagggcatc    3420
attggttcca ccccccacccc cctcgaaggt tatcccattc tcaccaacag tcatgccgcg    3480
tccctcacct tcaacagctt aggttacaga gcttgcacca taagctctag ccaaggcctc    3540
actctccctg accccctgccc catcgttctg gacaactaca ccaagtacct ctcatcctcc    3600
aactgcctcg tcgcgctcac cagatccaga actggcatcc agttcatggg ccccacaatg    3660
tacgttggag gttccaacgg gtcctccgca atgttctccg atgccatcaa ccacactccc    3720
atatcgatgg accgctactt tccggcccctc tttccatccc tcaacctcct tcacacccct    3780
ctcacctcca ggcgcgttcg tctcactgga gccaccccca gctccgtccc agccttcaga    3840
ccacccaatt ctggagccac cccccatctcc gtcccagcct tcagaccacc taatttccac    3900
```

```
cttcccccc acgtcccact ggactccagc cacgacttcg ttgccgtcaa cccacttctg    3960
gacgcctctg cctctgaatc ccgcctggac acccacttcc ttcctccgtc tcgcctcccc    4020
ctccacttcg acctcgctca aagccacacc cctcccccca cttattccca gacttctcct    4080
acagtcccaa tggccactgc ctgctaccct ggcgaaaatt ttgaaagttt ggccgcattc    4140
ttccttccag cccacgaccc ttctcttcgt gaaatttcct tccacgacca gacaagcaac    4200
caattccctt ggtctgatcg ccctttctca ctctcctgcc aacctccag tctcatcgca    4260 gccaaacatt cccccgccgc cgatccgacg ctcctcccgg cctccatcaa caaaagactt    4320
cgtttcaggc cgaatgacgc gcctcacgcc atcaccgccg atgatgtcat cctaggcctc    4380
caactcttcc aatccctttg ccgagcgtac catcgcacgc cctcccagtc cgttcctttc    4440
aacccagagc tgttcgctga gtgcatctcc ctcaacgagt atgcccagct cagctccaaa    4500
acccaggcaa ccatagtcgc caacgcctct cgttccgacc ccgactggcg acacactacc    4560
gtcaagatct tcgccaaggc ccagcacaaa gtgaacgatg gctcaatctt cggaccttgg    4620
aaagcttgcc agaccctcgc tttgatgcac gacttcgtca ttctcgtcct cggccctgtc    4680
aagaaatatc agcggatatt tgacaaccac gaccgcccat ctcacatcta cacccactgc    4740
ggcaaaacac caatccaact taacgattgg tgccagctca acctcacttc caacactcca    4800
aaaatcgcca atgattacac agccttcgac cagtctcaac atggcgagtc cgtggtcctt    4860
gaagccctta aaatgaaacg actgaacatc ccccccatc tcattgaact ccatgttcat    4920
ctcaaaacca acgtcagcac ccaatttggc ccgcttacct gcatgcgcct cacggggag    4980 cccgggacct acgacgacaa cacggactac aacttggccg tgattttctc ccaatacgaa    5040
gtcggctctt gcccaatcat ggtttccggc gacgactccc tcatcgaccg cgcactcccc    5100
atgcgccatg actggcctgt tgttctaaag cgcctgcacc tcaagttcaa acttgaacac    5160
acagaccacc cccttttctg cggctactat gtgggcccc ccggttgcat tcgcagtcct    5220
ctcgcactct tctgcaagct gatgatagcg gtggacgatg acgccctccc tgacagacgc    5280
ttgagttacc tcacggaatt cacaactggc catcgcttag gggaggccct ctgggaattg    5340
ctcccacccg agttaaccaa gtttcaaagc gcctgctttg atttcttctg ccgccactgc    5400
cccaaacacg aaaagatgct cctcagcgat gaacctcccc aatcctcaat tctggagcgc    5460
ctcacatcct cctcaaaatg gctctccaaa acgccatgt acctcttacc aaccaagttg    5520
cgtctcgcca ttctcaactt ctctcagact caatccctcc cggaatccct tgaagtttct    5580
cagcttgagt ctgaattgct tcaccacctt caatagcaac cagccccaac atggatgtcg    5640
acaaggagct cgcccccca gaccaaactc tcaccgtccc aaccgtccta ccccttcccg    5700
ctggcgccac tcctcccgtc atcaaacaag tctttcaatc tgaaatcttg ttcgctggca    5760
ccaaagacgc tgaggcctcg atcaccatcg ccaatctcga cagcgtcacc aacctcacct    5820
ctctctaccg ccacgcctct ctcgactccc tctgggtcac aattcacccc actctccaag    5880 caccccgcatt cccaacaact gttggtatct gctgggtctc cgcaaaatca cccatcaact    5940
ccgcacaaat caccaaaacc tttggtggtc agatttttctg catcggcgga tccatcaaca    6000
ccctccaacc cctcgtgatt cattgcccac tctcaatgat gaatcgacga gtcaaagact    6060
ccattcaata ccttgactcc cccaaactca ttctctctat caccgcacag cccaccgccc    6120
ctcccgcatc aacctgtata ataactgtct caggttccat ctccatgcac tctccgctcc    6180
ttgcggacac ttctctctaa gttctcgatc tttaaaatcg ttagctcgcc agttagcgag    6240
```

```
gcctgttccc acacaacagg tattcgggtg caactcccgc ctccttccga gggtcatcgg    6300
aacc                                                                 6304

<210> SEQ ID NO 2
<211> LENGTH: 23
<212> TYPE: DNA
<213> ORGANISM: Artificial Sequence
<220> FEATURE:
<223> OTHER INFORMATION: AV F primer

<400> SEQUENCE: 2
ccctgctcct actcacaatc tcc                                              23

<210> SEQ ID NO 3
<211> LENGTH: 20
<212> TYPE: DNA
<213> ORGANISM: Artificial Sequence
<220> FEATURE:
<223> OTHER INFORMATION: AV R primer

<400> SEQUENCE: 3
agctttcctc tcccacatca                                                  20

<210> SEQ ID NO 4
<211> LENGTH: 17
<212> TYPE: DNA
<213> ORGANISM: Artificial Sequence
<220> FEATURE:
<223> OTHER INFORMATION: AV TM probe

<400> SEQUENCE: 4
ctaccatcgc cacatgc                                                     17
```

EXOGENOUS INTERNAL POSITIVE CONTROL

CROSS REFERENCE TO RELATED APPLICATIONS

This application is a U.S. National Phase patent application of PCT/IB2012/050859, filed on Feb. 24, 2012, which claims priority to U.S. Provisional Application No. 61/463,980, filed Feb. 25, 2011, the disclosures of which are hereby incorporated by reference in the present disclosure in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002129300SeqList.txt, date recorded: Nov. 17, 2014, size: 9 KB).

TECHNICAL FIELD

The present invention relates to the use of a second virus as an exogenous internal positive control in methods for verifying the reliability of an assay to detect a first virus, in methods of ensuring the absence of the first virus in a biological sample or pharmaceutical sample and in methods of manufacturing a vaccine free from a first virus.

BACKGROUND OF THE INVENTION

Viral contamination in biological samples is a problem in a number of areas of medicine including blood transfusion and organ transplantation, and vaccine and drug production. Viruses can be detected in biological samples using a number of different tests that detect the presence of viral antigens, host antibodies to viral antigens or viral nucleic acids.

When testing a biological sample for contamination by a virus or confirming that a biological sample is free from a virus, a problem exists with interpreting a negative result. Without appropriate controls, it is not possible to determine whether an absence of contaminating virus being detected is as a result of the failure of the assay, or as a result of the absence of any contaminating virus in the biological sample. If the negative result can be attributed to the former reason, the failure of the assay could have occurred at any stage. For example, in a nucleic acid assay, the failure may have occurred during nucleic acid extraction, handling, amplification or detection steps. Generally, four controls are used in PCR based methods for the detection of viral nucleic acids. The first control is an internal positive control for the nucleic acid extraction step. The second control is for the detection of the PCR products. The third control is for the amplification step. Finally, the fourth control is a no template control to detect contamination during the assay. Similar controls are used in assays to detect viral polypeptides.

The present invention relates to the use of a second virus as an exogenous internal positive.

The concept of using an exogenous virus as an internal positive control for diagnostic purposes is known in the art. For example, Mairhofer et al. (*qPCR 2007 Symposium & Exhibition & Workshop* 3rd International qPCR Symposium, page 28. ISBN-13 978-3-00-020385-5) describes the use of Tomato Mosaic Virus (ToMV) as an internal positive control in an assay for the detection of influenza A virus in a biological sample from a subject infected with influenza A. This system, however, has several disadvantages. In particular, ToMV did not work as an internal positive control for the detection of Norovirus I from clinical specimens and its use as an internal positive control is therefore limited.

A further disadvantage of the system described by Mairhofer et al. is that the control virus (ToMV) and the test virus (influenza A) are different types of virus. ToMV is a non-enveloped virus with a +ssRNA genome. On the other hand, influenza A is an enveloped virus with a −ssRNA genome. This is likely to lead to a lack of reliability of the positive control. For example, if extraction, amplification and detection steps are optimised for the positive control virus it is possible that the conditions in any one of the extraction, amplification and detection steps would not be suitable for the contaminating virus. Thus, a negative result for the detection of the contaminating virus when the assay is positive for the detection of the control virus could represent a failure of the extraction, amplification or detection step to work for the contaminating virus rather than an absence of contamination in the biological sample. Indeed, Mairhoffer et al. reported at the 2007 qPCR symposium that ToMV and Norovirus nucleic acids can not both be detected in a same sample known to contain both viruses when the nucleic acids are extracted under the same conditions.

A yet further disadvantage of the use of ToMV is that the virus is commonly found in all solenaceous plant (for example tobacco, potato and tomato). Thus, contamination of the assay with the positive control after nucleic acid extraction is possible from commonly found plant materials. If a sample were to be contaminated after the nucleic acid extraction step, a positive result for the detection of the control virus ToMV could result even if the extraction step failed.

There therefore remains a need for a suitable internal positive control for nucleic acid extraction and detection assays. To our knowledge, the use of exogenous viruses as an internal positive control (IPC) in vaccine manufacturing has not been described previously.

DISCLOSURE OF THE INVENTION

The present invention relates to the use of a second virus as an internal positive control in an assay to detect a first virus in a biological sample. The second virus can be added to the biological sample prior to carrying out an assay to detect the first and second viruses.

In a particular embodiment, the present invention relates to an internal positive control for in nucleic acid extraction (Ex-IPC) and nucleic acid detection assays. The invention relates to the use of a second virus or viral nucleic acid as an exogenous internal positive control in nucleic acid extraction and nucleic acid detection assays for the detection of a first virus, in which the second virus used as the internal positive control could not be present in the biological sample other than when added exogenously.

The present inventors have found that when the first and second viruses are of the same type, the second virus can act as an internal positive control for the nucleic acid extraction step in an assay to determine the presence or absence of contamination of a biological sample by the first virus.

The invention therefore provides:
- methods for verifying the reliability of an assay to detect a first virus
- methods for confirming that a biological sample is substantially free from a first virus methods for testing blood and/or a blood product for the presence or absence of a first virus methods for testing a vaccine or intermediate in the manufacture of a vaccine for the presence or absence of a first virus use of a second virus as an internal positive control in an assay to detect a first virus in a biological sample kits for the detection of a first and second viral nucleic acids or polypeptides in a biological sample wherein the second virus is an internal positive control primers and probes for the detection of *Alliaria petiolata* tymovirus vaccines, intermediates in the manufacture of vaccines, blood and/or blood products that have been confirmed to be free from the presence of a first virus methods of manufacturing a vaccine that is free from a first virus in methods for testing for the presence or absence of a virus of interest in a composition, the improvement consisting of adding an exogenous control virus to the composition, wherein the control virus and the virus of interest are of the same type of virus.
- in methods for manufacturing a biological and/or pharmaceutical product, the improvement consisting of adding an exogenous control virus to a sample of the product in order to test it for viral contamination, wherein the control virus and the virus of interest are of the same type of virus.

Methods of the Invention

In one embodiment, the invention provides a method for verifying the reliability of an assay to detect a first virus comprising the steps of:

(a) adding an exogenous second virus to a biological sample prior to analysing the nucleic acids from the biological sample; and (b) analysing the nucleic acids from the biological sample to detect the first and second virus;

wherein the first and second virus are the same type of virus.

The methods may contain a further step of extracting nucleic acids from the biological sample prior to analysing the extracted nucleic acids. In this embodiment, the invention provides a method for verifying the reliability of an assay to detect a first virus comprising the steps of:

(a) adding an exogenous second virus to a biological sample prior to extracting nucleic acids from the biological sample;

(b) extracting nucleic acids from the biological sample; and (c) analysing the nucleic acids from step (b) to detect the first and second virus;

wherein the first and second virus are the same type of virus.

The analysing step may comprise nucleic acid amplification and detection steps.

By "verifying the reliability" of an assay, it is meant that the second virus can act as a positive control for a nucleic acid extraction step and/or analysis step. Detection of the second virus in the analysis step indicates that the nucleic acid extraction step (where present) succeeded. Absence of detection of the second virus indicates that the nucleic acid extraction step (where present) failed, or that the analysing step failed.

Further controls may also be used in the methods of the present invention, including further positive controls for the analysing step, for example a positive control for the nucleic acid amplification step and a positive control for the nucleic acid detection step, and a negative control or no template control which contains no detectable nucleic acids. These further controls can be used to determine whether failure to detect the second virus in the analysing step is due to a failure of the nucleic acid extraction step (where present) or the analysing step.

In a further embodiment, the invention provides a method of confirming that a biological sample is substantially free from a first virus, comprising the steps of:

(a) adding an exogenous second virus to a biological sample prior to analysing nucleic acids from the biological sample;

(b) analysing nucleic acids from the biological sample to detect the first and second virus; and (c) detecting presence of the second virus but absence of the first virus;

wherein the first and second virus are the same type of virus.

The methods may contain a further step of extracting the nucleic acids from the biological sample prior to analysing the extracted nucleic acids. In this embodiment, the invention provides a method of confirming that a biological sample is substantially free from a first virus, comprising the steps of:

(a) adding an exogenous second virus to a biological sample prior to extracting nucleic acids from the biological sample;

(b) extracting nucleic acids from the biological sample;

(c) analysing the nucleic acids from step (b) to detect the first and second virus; and (d) detecting the presence of the second virus but the absence the first virus;

wherein the first and second virus are the same type of virus.

The invention also provides the use of a second virus as an internal positive control in an assay to detect a first virus in a biological sample, wherein the first and second viruses are the same type of virus.

By "same type of virus" it is meant that the first and second viruses have the same structure and/or genome type. In one embodiment, both viruses may have the same structure, e.g. both viruses may be enveloped or non-enveloped viruses. Alternatively, or in addition, the viruses may have the same structure of capsid, e.g. both viruses may be filamentous viruses (also referred to in the art as helical viruses), icosahedral viruses or complex viruses that possess a capsid that is neither purely filamentous, nor purely icosahedral. Additionally or alternatively, both viruses may have the same genome type, e.g. both viruses may be dsDNA viruses, ssDNA viruses, dsRNA viruses, +ssRNA viruses, −ssRNA viruses, ssRNA retroviruses or dsRNA retroviruses. The viral genomes of both viruses may be linear or circular, and may be segmented or may be a single nucleic acid. In the case of a segmented genome, each virion may contain one or more genome segments.

In one particularly advantageous embodiment, the first and second viruses have different, non-overlapping host ranges. As an example, a biological sample from a subject of a first animal species, which may contain a first animal virus (among other animal viruses that can infect the first species), will not naturally contain the control, second virus if that second virus can not infect the first animal species. In one particular embodiment, the first virus is an animal virus, e.g. a mammalian virus or an avian virus, and the second virus is a plant virus. In a particular embodiment, the mammal is a human. In a further particular embodiment, the avian virus is a virus that infects poultry, for example chickens, turkeys and/or ducks. In these embodiments there can be no overlap in host range.

Plant viruses are particularly advantageous as a second virus IPC in vaccine manufacture, for the detection of a first virus that may contaminate a vaccine. The particular advantages of using a plant virus as an IPC include the safety of the virus—a plant virus is non-pathogenic to workers involved in vaccine manufacture; the reliability of the assay—unlike a second human or mammalian virus, a worker involved in vaccine manufacture is not likely to be contaminated with a plant virus, particularly if that plant virus does not infect plant species that commonly come into contact with humans; and cost—a large number of plant viruses can be easily and cheaply produced in plant cell culture.

The invention also provides a method of selecting an IPC for an assay for the detection of a first virus comprising:

(a) selecting a first virus;
(b) determining the virus type for the first virus;
(c) selecting a second virus of the same type with a non-overlapping host range; and
(d) confirming that both the nucleic acids of the first and second viruses can be extracted from a biological sample using the same extraction procedure and/or that the nucleic acids from the first and second viruses can be detected using the same nucleic acid analysing step.

In general terms, the first virus is a virus of interest, whose presence or absence needs to be tested, confirmed or verified (typically a human pathogen), and the second virus is a control virus (typically not a human pathogen). Specific examples of pairs of viruses suitable for use in the present invention include the following:

| First Virus | Second Virus |
|---|---|
| Poxvirus | Chlorella virus |
| Hepatitis B virus | Cauliflower Mosaic Virus |
| Circovirus | Nanovirus |
| Picornavirus, in particular Polio virus | Dandelion yellow mosaic virus |
| Mammalian or avian reovirus or Norovirus | *Alliaria petiolata* tymovirus |

In one embodiment, the plant virus is not a commonly occurring plant virus, such as a virus that infects crop plants like wheat, tomato, tobacco, maize, etc. In a preferred embodiment, the second virus is *Alliaria petiolata* tymovirus (ApTV). This virus was isolated by Prof. Artur Pfitzner in 1997 in Stuttgart-Möhringen, Germany from *Alliaria petiolata* plants which showed typical signs of virus infections (mosaic leaves). Sequencing of the whole genome by the University of Hohenheim, Department of General Virology revealed that the newly isolated virus belongs to the family of tymoviridae, genus tymovirus (+ssRNA, non-enveloped, isometric, icosahedral viruses). The genome sequence is given in SEQ ID NO: 1 (in DNA form). Although the existence of ApTV was known (Ohnesorge S., et al (1998) Isolation und Charakterisierung eines neuen Tymovirus aus *Alliaria officinalis*—Jahrestagung der Deutschen Virologischen Gesellschaft, Regensburg; Ohnesorge S. (1999) Interaktion und subzelluläre Lokalisation von Homeodomän-Transkriptionsfaktoren aus *Arabidopsis thaliana*—Dissertation an der Fakultät für Biologie Universität Hohenheim; Ohnesorge S., Pfitzner A. J. P. (2003) Isolation and Characterization of a new Tymovirus from *Alliaria petiolata*—Jahrestagung der Deutschen Virologischen Gesellschaft, Tübingen), this sequence is currently unpublished.

More generally, the second virus may be any virus in the Tymoviridae family, including any such virus in the Tymovirus, Maculavirus or Marafivirus genus. For example, it may be a turnip yellow mosaic virus, an Andean potato latent virus, a belladonna mottle virus, a cacao yellow mosaic virus, a clitoria yellow vein virus, a desmodium yellow mottle virus, a dulcamara mottle virus, an eggplant mosaic virus, an erysimum latent virus, a kennedya yellow mosaic virus, a melon rugose mosaic virus, an okra mosaic virus, an ononis yellow mosaic virus, a passionfruit yellow mosaic virus, a physalis mottle virus, a plantago mottle virus, a scrophularia mottle virus, a voandzeia necrotic mosaic virus, a wild cucumber mosaic virus, or an belia latent virus.

ApTV is particularly useful as a second virus for use as a control with the invention because its host, *Alliaria petiolata*, is not grown as a crop plant. Thus, contamination from *Alliaria petiolata* tissue containing ApTV is extremely unlikely in the biological samples of interest. For example, an individual from whom a biological sample is obtained is much less likely to have come into contact with contaminated *Alliaria petiolata* than a tomato, potato or tobacco plant or plant product contaminated with ToMV. The restricted host range of this virus also leads to a low risk of environmental contamination.

In particular embodiments, ApTV is useful as an internal positive control for in methods for the detection of a first non-enveloped and/or icosehedral and/or +ssRNA virus. In a preferred embodiment, ApTV is used as the second, control virus in an assay to detect the presence of a first mammalian or avian reovirus, which is a non-enveloped, icosehedral, dsRNA virus. The mammalian reovirus (MRV) may be any type of strain of MRV e.g. MRV-1, MRV-2 and/or MRV-3.

The exogenous second virus may be added to the biological sample at a concentration of about 50-300 pg/ml. For example, the concentration of the second virus added to the biological sample may be about 50, 100, 150, 200, 250 or 300 pg/ml.

In a further aspect of the invention the methods rely on the detection of viral polypeptides rather than viral nucleic acids. In this aspect, one embodiment of the invention is a method for verifying the reliability of an assay to detect a first virus that comprises the steps of:

(a) adding an exogenous second virus to a biological sample prior to analysing viral polypeptides from the biological sample; and
(b) analysing viral polypeptides from the biological sample to detect the first and second virus;

wherein the first and second virus are the same type of virus.

In a further embodiment of this aspect of the invention, the invention provides a method of confirming that a biological sample is substantially free from a first virus, comprising the steps of:

(a) adding an exogenous second virus to a biological sample prior to analysing viral polypeptides from the biological sample;
(b) analysing viral polypeptides from the biological sample to detect the first and second virus; and
(c) detecting the presence of the second virus but the absence the first virus;

wherein the first and second virus are the same type of virus.

The invention also provides a method for analysing a composition, comprising steps of (a) adding a control virus to a sample of the composition, then (b) testing the sample for the presence of a virus of interest, wherein the control virus and the virus of interest are different from each other but are the same type of virus. In addition to performing step (b), the method will typically include a step of testing the sample for the presence of the control virus. Thus the method provides a useful positive control for verifying tests for the virus of interest.

Viral Nucleic Acid Analysis

The analysing step in the methods of the present invention can be used to identify the presence or absence of a nucleic acid originating from the first and/or second virus. A positive result is the detection of the presence of a nucleic acid. A negative result is the absence of detection of a nucleic acid. Given that the present invention is directed in part to ensuring that biological samples are free from contamination from viruses, it is anticipated that the assays of the invention will predominantly be used to detect or confirm the absence of viral nucleic acids.

Nucleic acids can be extracted from a biological sample, and in particular from the viral particles contained within the biological samples, by any method known in the art. In one embodiment, the nucleic acids are isolated from virus particles using the commercially automated RNA/DNA system MagNA Pure Compact System (Roche) with the MagNA Pure Compact Nucleic Acid Isolation Kit (Roche). Alternatively, the RNA/DNA can be isolated from the virus particles using the commercially available QIAsymphony Midi Virus/Bacteria Kit. Virus particles may be lysed by incubation of the samples with lysis buffer containing proteinase K.

Preferably, the nucleic acid extraction procedure should extract nucleic acids from the first and second viruses with comparable efficiency.

In some embodiments of the invention a nucleic acid extraction step is not required. The nucleic acids in the biological sample may be analysed directly without any prior extraction step, for example as described in Pannacio et al. (Nucleic Acids Res. 1993 Sep. 25; 21(19): 4656) and Pandori et al. (BMC Infect Dis. 2006 Jun. 24; 6:104).

For the analysis, a nucleic acid assay is conducted. The analysing step of the methods of the invention may involve nucleic acid amplification and nucleic acid detection steps.

A preferred assay for detection of RNA viruses is Reverse Transcriptase Polymerase Chain Reaction (RT-PCR). However, equivalent RNA amplification methods are also applicable, as known to the person skilled in the art (Nucleic Acid Sequence Based Amplification or NASBA™ as in U.S. Pat. No. 5,409,818; 3SR™; Transcription Mediated Amplification or TMA™ as in U.S. Pat. No. 5,399,491 etc.). In the present invention, the reverse transcription reaction or equivalent RNA amplification method can be carried out on single-stranded viruses, or on the positive strand, the negative strand or both strands in double stranded viruses. Thus, the methods of the invention can be used to detect the positive and/or negative strand of the first and second viral genomes.

In a particular embodiment, a one step RT-real time PCR assay is used ("one step RT-qPCR"). The person skilled in the art is familiar with conducting such "one step RT qPCR" assays. He knows how to find detailed reaction conditions for such amplification. The reverse transcription reaction (RT) and the amplification reaction (qPCR) may be performed in the same vessel (e.g. in a single tube or vial) rather than in separate vessels.

Commercially available RT-PCR kits can be used, e.g. Qiagen QuantiTect™ Virus kit or Invitrogen Super Script™ III Platinum™ kit. The generated fluorescence signals can be analysed using the respective real time cycler software, as known in the art.

A preferred assay for detection of DNA viruses is Polymerase Chain Reaction (PCR). However, any nucleic acid amplification methods are also applicable, as known to the person skilled in the art.

The nucleic acid assay is preferably run as a real time assay (e.g. "qPCR"; Taqman™, Lightcycler™; Scorpion™ etc.).

In one embodiment, the invention provides primer and probe sequences for the detection of ApTV in the methods and kits of the present invention. When the second virus is ApTV primers for the nucleic acid assay of the invention can be any nucleic acid sequence of about 10-60 bases in length, e.g. 10-30 bases in length, more specifically 10, 11, 12, 13, 14, 15, 16, 17, 18, 19, 20, 21, 22, 23, 24, 25, 26, 27, 28, 29 or 30 bases in length, which hybridises to the ApTV genome (SEQ ID NO: 1) or the complement thereof with a Tm of ≥50° C., preferably 50° C.-75° C., or 55° C.-65° C., in the presence of 50 mM monovalent cations. In a particular embodiment, the primer comprises a nucleic acid sequence which is a fragment of SEQ ID NO: 1 or the complement thereof, wherein the fragment is about 10-30 bases in length, e.g. 10, 11, 12, 13, 14, 15, 16, 17, 18, 19, 20, 21, 22, 23, 24, 25, 26, 27, 28, 29 or 30 bases in length.

In any particular primer pair, a first primer, referred to as the forward primer, will hybridise with the ApTV genome and the second primer, referred to as the reverse primer, will hybridise with the complement of the viral genome. In one embodiment, the ΔTm of any particular primer pair comprising one forward and one reverse primer is ≤about 5° C., e.g. about 5° C., 4° C., 3° C., 2° C., 1° C. or less.

In one embodiment, the primers for use in the methods and kits of the present invention are designed so that the fragment amplified by a specific primer pair is ≤about 150 bases in length, e.g. from about 150 to about 50 nucleotides long including the primer sequences. In a specific embodiment, the amplified fragment may be about 140 bases, 130 bases, 120 bases, 110 bases, 100 bases, 90 bases, 80 bases, 70 bases, or 60 bases long including the primer sequences.

The invention also provides probe sequences for detecting the amplified PCR product, for use in the methods and kits of the present invention. Probe sequences are about 10-60 bases in length, e.g. 20-40 bases in length, more specifically 20, 21, 22, 23, 24, 25, 26, 27, 28, 29 or 30 bases in length, and hybridise with the ApTV genome (SEQ ID NO: 1) or its complement with a Tm of ≥50° C., preferably 50° C.-75° C., or 55° C.-65° C., in the presence of 50 mM monovalent cations.

In a particular embodiment, the probe comprises a nucleic acid sequence which is a fragment of SEQ ID NO: 1 or the complement thereof. The fragment may be 10-60 bases in length, e.g. 20-40 bases in length, more specifically 20, 21, 22, 23, 24, 25, 26, 27, 28, 29 or 30 bases in length.

Primers and/or probes (e.g. SEQ ID NOs: 2-4) may be labeled e.g. with a radiolabel, a fluorescent label such as 5' 6-carboxyfluorescein (6FAM) label and/or a 3' 'BlackBerry Quencher' (BBQ) label or any other label known in the art. Probes may be locked nucleic acid (LNA) oligonucleotides that contain a cytosine modified with a 2'-O, 4'-C methylene bridge in its ribose conferring enhanced hybridization performance.

The invention also provides nucleic acids which comprise a nucleotide sequence selected from SEQ ID NOs: 2, 3 and 4 for use in the methods and kits of the present invention. These nucleic acids should be single-stranded with a length of less than 80 nucleotides e.g. less than 50 nucleotides, or less than 30 nucleotides. They can be useful as primers and/or probes for detecting MRV. The nucleic acid may have the same 3' residue as the relevant SEQ ID NO: i.e. it may comprise a sequence 5'-X-Y-3' where: Y is a sequence selected from SEQ ID NOs 2, 3 and 4; and X is a nucleotide sequence of 1 or more nucleotides. The nucleic acid with sequence 5'-X-Y-3' can hybridize to an ApTV nucleic acid.

Viral Polypeptide Analysis

The analysing step in the methods of the present invention can be used to identify the presence or absence of a polypeptide originating from the first and/or second virus. A positive result is the detection of the presence of a viral polypeptide. A negative result is the absence of detection of a viral polypeptide. As the present invention is directed in part to ensuring that biological samples are free from contamination from viruses, it is anticipated that the assays of the invention will predominantly be used to detect or confirm the absence of viral polypeptides.

Various techniques are available for detection of proteins, including but not limited to immunoblotting (e.g. western blotting), immunoprecipitation, immunoelectrophoresis, mass-spectrometry, immunodiffusion (e.g. SRID), immunochemical methods, binder-ligand assays (e.g. ELISA), immunohistochemical techniques, agglutination assays, etc.

Immunoassay methods are preferred, in which protein is detected by using one or more antibodies. Antibodies useful in these methods may be specific for any part of a viral protein (typically a structural protein) but are ideally specific for a sequence which is well conserved between different isolates. Various immunoassay formats are available to the skilled person and these often involve the use of a labeled antibody e.g. with an enzymatic, fluorescent, chemiluminescent, radioactive, or dye label. Assays which amplify signals from immune complexes are also known e.g. those which utilize biotin and avidin, and enzyme-labeled and mediated immunoassays, such as ELISA.

The "antibody" used in these methods can take various forms. Thus the antibody may be a polyclonal or monoclonal preparation. For specificity and reproducibility reasons it is preferred to use a monoclonal antibody. The antibody may be native antibodies, as naturally found in mammals, or artificial. Thus the antibody may be, for example, a fragment of a native antibody which retains antigen binding activity (e.g. a Fab fragment, a Fab' fragment, a F(ab')$_2$ fragment, a Fv fragment), a "single-chain Fv" comprising a $V_H$ and $V_L$ domain as a single polypeptide chain, a "diabody", a "triabody", a single variable domain or VHH antibody, a "domain antibody" (dAb), a chimeric antibody having constant domains from one organism but variable domains from a different organism, a CDR-grafted antibody, etc. The antibody may include a single antigen-binding site (e.g. as in a Fab fragment or a scFv) or multiple antigen-binding sites (e.g. as in a F(ab')$_2$ fragment or a diabody or a native antibody). Where an antibody has more than one antigen-binding site it is preferably a mono-specific antibody i.e. all antigen-binding sites recognize the same antigen.

An antibody may include a non-protein substance e.g. via covalent conjugation. For example, an antibody may include a detectable label.

The term "monoclonal" as originally used in relation to antibodies referred to antibodies produced by a single clonal line of immune cells, as opposed to "polyclonal" antibodies that, while all recognizing the same target protein, were produced by different B cells and would be directed to different epitopes on that protein. As used herein, the word "monoclonal" does not imply any particular cellular origin, but refers to any population of antibodies that all have the same amino acid sequence and recognize the same epitope(s) in the same target protein(s). Thus a monoclonal antibody may be produced using any suitable protein synthesis system, including immune cells, non-immune cells, acellular systems, etc. This usage is usual in the field e.g. the product datasheets for the CDR-grafted humanised antibody Synagis™ expressed in a murine myeloma NSO cell line, the humanised antibody Herceptin™ expressed in a CHO cell line, and the phage-displayed antibody Humira™ expressed in a CHO cell line all refer the products as monoclonal antibodies. The term "monoclonal antibody" thus is not limited regarding the species or source of the antibody, nor by the manner in which it is made.

Antibodies used with the invention ideally bind to epitopes inside a polypeptide encoded within SEQ ID NO: 1. Suitable epitopes can be identified in vitro or in silico using conventional epitope prediction and mapping techniques. Once identified, an epitope can be confirmed as non-cross-reactive with another virus of interest.

An immunoassay may be, without limitation, in a heterogeneous or in a homogeneous format, and of a standard or competitive type.

The invention provides antibodies that specifically bind to ApTV polypeptides for use in the methods of the invention. In one embodiment, the invention provides antibodies that bind specifically to one or more of the polypeptide encoded by SEQ ID NO: 1. By "binds specifically", it is meant that the antibodies bind to a polypeptide encoded by SEQ ID NO: 1 with substantially greater affinity than BSA. Preferably, the affinity is at least 100-fold, $10^3$-fold, $10^4$-fold, $10^5$-fold, $10^6$-fold etc. greater for the polypeptides of the invention than for BSA.

In one embodiment, the antibodies bind to the polypeptides encoded by SEQ ID NO: 1 with at least a 10-fold, 100-fold, $10^3$-fold, $10^4$-fold, $10^5$-fold, $10^6$-fold etc. greater affinity than its binding affinity to a any viral polypeptide.

The polypeptides encoded by SEQ ID NO: 1 which bind specifically to the antibodies of the invention are referred to as antigens.

Biological Samples

The present invention is suitable for use with any biological sample. For example, clinical samples are frequently tested for the presence of a particular virus. Thus the biological sample may be blood or blood products such as: whole blood; blood fractions; blood components such as serum, plasma, red blood cells, white blood cells and/or platelets; a coagulation factor concentrate, serum albumin, or an immunoglobulin preparation. In one particular embodiment, the blood or blood product may be from or destined for a blood bank and/or use for blood transfusion.

The invention can also be used for non-biological samples which might be contaminated with viruses. For example, the sample might be a pharmaceutical product.

The sample may be a heat-inactivated sample, or a sample from a heat-inactivated product.

The biological sample may also be any tissue sample or biopsy, including but not limited to bone marrow, kidney, liver, heart, lung, and/or skin. The biological sample may also be urine, fecal matter, sputum, saliva, aspirate, pharangeal wash, bronchiolar lavage, amniotic fluid, synovial fluid, follicular fluid, ascites fluid and/or cerebrospinal fluid.

In this embodiment, the invention provides a method for testing blood and/or a blood product for the presence or absence of a first virus comprising the steps of:

(a) taking a sample of the blood and/or blood product
(b) adding an exogenous second virus to the sample; and
(c) detecting the presence of the second virus and the presence or absence of the first virus using a method or kit of the present invention;

wherein the first and second virus are the same type of virus.

The invention also provides blood or a blood product that has been confirmed to be free from a first virus using the methods or kits of the invention.

Blood products which can be tested using the invention include, but are not limited to: whole blood; plasma (e.g. apheresis plasma or recovered plasma); serum; platelets; blood plasma products; coagulation factor concentrate; coagulation factors such as factors VII, VIII, IX, or factor VIII/vWF; activated prothrombin complex concentrate (APCC) serum albumin, including human serum albumin; or immunoglobulin preparations. The product may be a heat-inactivated product.

Any suitable first and second virus pair may be used in this embodiment of the invention. In particular, where the first virus is MRV, the second virus may be ApTV.

In a further embodiment, the biological sample is a vaccine or intermediate in vaccine production (or a sample thereof). In a particular embodiment, the biological sample is an intermediate from influenza vaccine production or an influenza vaccine. The influenza vaccine may be produced in embryonated eggs or in cell culture.

In particular, the cell-culture based influenza vaccine production or an influenza vaccine may be the Optaflu™ process and vaccine described e.g. in WO 2008/068631. The most preferred cell lines for growing influenza viruses are MDCK cell lines. The original MDCK cell line is available from the ATCC as CCL-34, but derivatives of this cell line and other MDCK cell lines may also be used. For instance, in WO97/37000 a MDCK cell line is disclosed that was adapted for growth in suspension culture ('MDCK 33016', deposited as DSM ACC 2219). Similarly, WO01/64846 discloses a MDCK-derived cell line that grows in suspension in serum-free culture ('B-702', deposited as FERM BP-7449). WO2006/071563 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). WO2005/113758 discloses MDCK cell lines with high susceptibility to infection, including 'MDCK.5F1' cells (ATCC CRL-12042).

The cell culture based vaccine production process usually comprises the following steps: The starting material for each monovalent bulk is a single vial of the MDCK working cell bank (WCB). The cells are propagated in a chemically defined medium to optimize cell growth during production. The WCB are expanded by sequential passage in spinner flasks followed by scale up in larger fermentation vessels. Seed virus is added and virus propagation in the fermenter is performed over a period of two to four days. At the end of the infection cycle, the virus suspension is centrifuged and filtered to remove residual intact cells from the culture harvest. The centrifuged, filtered bulk termed clarified virus harvest is the end of the fermentation process. The clarified virus harvest may be stored at room temperature (16-25° C.) in a stainless steel storage vessel for up to 24 hours. The influenza virus is purified by chromatography and ultra-/diafiltration steps, inactivated by beta-propiolactone (BPL) and disrupted by cetyltrimethylammonium bromide (CTAB) to solubilize the viral surface antigens HA and NA. The drug substance production process concludes with a filtration of the concentrate into the final bulk vessel to obtain monovalent bulk. Finally, the monovalent bulks can be blended into multivalent bulks (typically trivalent bulks) and filled into their final container, e.g. syringes. It is standard practice to minimize the amount of residual cell line DNA in the final vaccine, in order to minimize any oncogenic activity of the DNA (see in detail WO 2008/068631).

The method of the invention may be performed at any stage(s) during vaccine manufacture, starting from the seed virus and/or the cell substrate and/or the culture medium, through the viral infection and growth stages, through viral harvest, through any viral processing (e.g. splitting and/or surface protein extraction), through vaccine formulation and then to vaccine packaging. Thus the assay used according to the methods of the invention can be performed on the materials used to create the viral culture, on the viral culture itself, and on material extracted and derived from the viral culture. The assay need not be performed on each and every vaccine or culture, but can be used at appropriate intervals as part of normal quality control. It is particularly useful when vaccine production is changed for the new yearly strains recommended by regulatory authorities, at which stage new cultures are established and must be subjected to new quality control. Methods of the invention are advantageously used when performing assays on the seed virus used for vaccine manufacture.

It is particularly important that any assay used in the quality control of vaccine production is robust, and not susceptible give false positive, false negative or variable results. The methods of the invention provide a robust means of assuring the reliability of the assay to detect a contaminating virus in a biological sample, in particular a vaccine or intermediate in the production of a vaccine.

In this embodiment, the invention provides a method for testing a vaccine and/or an intermediate in vaccine production for the presence or absence of a first virus comprising the steps of:
    (a) taking a sample of the vaccine and/or intermediate in vaccine production;
    (b) adding an exogenous second virus to the sample;
    (c) detecting the presence of the second virus, and the presence or absence of the first virus, using a method or kit of the present invention;
wherein the first and second virus are the same type of virus.

The invention also provides a vaccine or intermediate in vaccine production that has been confirmed to be free from a first virus using the methods or kits of the invention.

The invention also provides a method of manufacturing a vaccine free from a first virus comprising the steps of:
    (a) adding an exogenous second virus to an intermediate in the production of a vaccine (or sample thereof) or to a bulk vaccine (or sample thereof);
    (b) detecting therein the presence of the second virus and the presence or absence of the first virus using a method or kit of the present invention; and
    (c) formulating a vaccine free from the first virus,
wherein the first and second virus are the same type of virus.

Preferred methods of manufacturing vaccines and vaccine formulations, for example influenza vaccines, are described in WO2006/027698, WO2007/052163, WO2008/032219, WO2010/092477 and WO2010/092476.

Methods of the invention do not have to be performed on a complete sample. Thus a sample can be obtained, and the method can be performed on a portion of the sample e.g. on portions of a biopsy, or on aliquots of a cell culture sample.

Kits

The invention also provides kits for the detection of the presence or absence of a first and second virus in a biological sample wherein the second virus is an internal positive control, comprising the second virus and primers and/or probes for the detection of the second virus. Optionally, the kit may further comprise primers and/or probes for the detection of the first virus.

In a particular embodiment, the kit comprises ApTV viral particles and primers and/or a probe for the detection ApTV. In a specific embodiment, the primers have the sequence as recited in SEQ ID NOs: 2 and 3 (AV F primer: 5' CCC TGC TCC TAC TCA CAA TCT CC 3'-SEQ ID NOs: 2 and AV R primer: 5' AGC TTT CCT CTC CCA CAT CA 3'-SEQ ID NO: 3), and the probe has the sequence as recited in SEQ ID NO: 4 (AV TM: LNA TaqMan probe 5' Cy5-CTA CCA TCG CCA CAT GC-BBQ 3' [LNA bases in bold]).

Kits of the invention may further comprise reagents for carrying out the nucleic acid assay including, but not limited to, reverse transcriptase, Taq polymerase, polymerase buffer, dNTPs, RNase-free water and random primers.

The invention further provides kits useful during the detection of the presence or absence of a virus other than ApTV in a biological sample, comprising (i) ApTV viral particles and (ii) antibodies for detection ApTV.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

Tm for primers and probes is calculated using the formula:

$$T_m = 81.5° C. + 16.6° C. \times (\log_{10} [Na^+] + [K^+]) + 0.41° C. \times (\% GC) - 675/N$$

Further general information on influenza vaccines, including strains, cell lines for growth, doses, combinations, formulations, etc. can be found in chapters 17 & 18 of *Vaccines*. (eds. Plotkin & Orenstein) 4th edition, 2004. ISBN 0-7216-9688-0. Further details on viruses, including details of viral structure and genome type, and life cycle during viral growth etc., can be found in Knipe & Howley *Fields Virology* (4th edition, 2001). ISBN 0-7817-1832-5.

MODES FOR CARRYING OUT THE INVENTION

Biological Samples

Different biological samples were used during the development phase of the MRV RTD-PCR (table 2). Additionally, three potential inhibitory substances were investigated, which could potentially interfere with the internal positive control.

TABLE 2

Investigated biological samples

| Batch | Influenza Strain | Serotype |
|---|---|---|
| Fermenter harvests (B1): | | |
| F110711_B1 | (A/Solomon Islands/3/06) | H1N1 |
| F110714_B1 | (A/Wisconsin/67/05) | H3N2 |
| F110717_B1 | (B/Malaysia/2506/4) | Victoria |

TABLE 2-continued

Investigated biological samples

| Batch | Influenza Strain | Serotype |
|---|---|---|
| Seed virus: | | |
| 522SSV0805 | (B/Florida/4/06) | Yamagata |
| 522SSV0809 | (A/Brisbane/59/07) | H1N1 |
| 522SSV0811 | (A/Uruguay/716/07) | H3N2 |

For the investigations of the influence of inhibitory substances on the performance of the RTD-PCR method, three different components were used. MDCK host cell DNA, soluble MDCK host cell proteins of a B1 supernatant and a concentrated influenza virus solution were selected as potential inhibitory substances. The MDCK host cell DNA was isolated from batch 22.09.05 (0.6×10$^7$ MDCK cells/ml; manufactured in the laboratories of the Cell Culture Technology (TDM)). To produce a concentrated influenza virus solution and soluble MDCK host cell proteins, the F110829 B1 sample was centrifuged for 2 hours at 55,000 g. The pellet was resuspended in 5 ml PF/CDM media.

The inhibitory substances and all investigated biological samples were characterized according to DNA, total protein content and influenza virus concentrations. The analytical data is summarized in table 3.

TABLE 3

Summary of the analytical data for the three inhibitory substances and the matrices that were used during this evaluation. The DNA, the protein content and influenza virus concentration are the average of three determinations.

| Inhibitory substances/matrices | DNA (ng/mL) | Protein (µg/mL) | Influenza viruses (copies/mL) |
|---|---|---|---|
| Inhibitory substances: | | | |
| Influenza viruses (F110829_B1) | 3937 | 1129 | 1.80 × 10$^{12}$ |
| MDCK host cell DNA | 86539 | ND | ND |
| Matrices: | | | |
| F110711_B1 | 1206 | 102 | 1.54 × 10$^{10}$ |
| F110714_B1 | 644 | 83 | 2.54 × 10$^{10}$ |
| F110717_B1 | 757 | 51 | 6.12 × 10$^9$ |
| Seed virus 522SSV0805 | 1014 | 56 | 9.79 × 10$^9$ |
| Seed virus 522SSV0809 | 1080 | 45 | 1.84 × 10$^{10}$ |
| Seed virus 522SSV0811 | 300 | 23 | 6.35 × 10$^9$ |

ND Not detectable

The Pico Green assay was used to quantify the DNA content of the inhibitory substances, the B1 and seed virus samples.

The total protein content of the inhibitory substances and the matrices used was determined by the µBradford method. The test principle is as for a normal Bradford but with low protein concentrations. The samples were pre diluted with PBS buffer and measured against a BSA standard curve at 595 nm absorption. The dye reagent is the quick start Bradford dye reagent (150 µl) from BioRad which was incubated with the samples (150 µl) for 15 minutes before measurement.

To quantify the influenza virus copy number in a sample, a quantitative one step RT-PCR was used. The samples were pretreated with 1.5 μl RNase A/T1 (3 μg RNase A and 7.5 U RNase T1) for 60 minutes at room temperature (about 22° C.) to digest free ssRNA in a sample to quantify only influenza RNA protected by virus particles. Afterwards, the RNA was extracted with a RNA specific nucleic acid kit (MagNA Pure Compact Nucleic Acid Isolation Kit I—Large Volume).

For the quantitative RT-PCR, 5 μl of sample was used. The influenza virus RNA was reverse transcribed (RT) and amplified (RT for 15 minutes at 50° C., Taq activation for 2 minutes at 95° C.) and detected by PCR (denaturing for 15 seconds at 94° C. for 45 cycles; annealing/elongation for 45 seconds at 45° C. for 45 cycles) using influenza A or influenza B specific primers and probes in a SmartCycler Cepheid. The samples were measured against a standard to quantify the influenza virus copy number. The standard is a ssRNA fragment that was synthesized and cloned into the KpnI and SacI sites of a T3/T7 transcription vector (pGA4-ampR). It was prepared as final ssRNA solutions of 10 ng/ml of ssRNA (1 ml per aliquot). To prevent a non-specific absorption of the low concentration of ssRNA to the tube, 100 ng/μl yeast tRNA in 1×TE (pH 8.0) was added.

The effect of the choice of biological sample on variability of repeat assays was evaluated. The duplicate determination of MRV-1 in three different B1 samples showed only slightly differences between the determinations with a standard deviation of 0.72 Ct-values for the 6-FAM probe and 0.17 Ct-values for the Cy5 probe, respectively (table 4).

TABLE 4

Ct-values of the evaluation of the influence of inhibitory substances in three different B1 samples. No significant difference was observed.

| Probe | F110711_B1 | F110714_B1 | F110717_B1 | Average | StDev |
|---|---|---|---|---|---|
| 6-FAM | 29.33 | 29.94 | 30.94 | 30.14 | 0.72 |
|  | 30.59 | 29.29 | 30.74 |  |  |
| Cy5 | 27.77 | 27.95 | 27.68 | 27.73 | 0.17 |
|  | 27.57 | 27.53 | 27.90 |  |  |

Primers, Probes and Reagents

To show the robustness of the primer and probe concentrations, slightly differences in the given concentrations were used. The investigated concentrations were 0.5, 0.6 and 0.7 μM for the MRV and ApTV primers (AV F primer: 5' CCC TGC TCC TAC TCA CAA TCT CC 3'-SEQ ID NOs: 2 and AV R primer: 5' AGC TTT CCT CTC CCA CAT CA 3'-SEQ ID NO: 3), 0.18, 0.20 and 0.22 μM for the MRV probe and 0.08, 0.10 and 0.12 μM for the ApTV probe. All combinations of the investigated concentrations were measured in duplicate.

The investigation of slight differences in the primer and probe concentrations showed a standard deviation below 0.7 Ct-values (table 5). Additionally, the maximal deviation from the mean Ct value was below 1.5 Ct-values.

TABLE 5

Results of the investigation of slightly differences in the primer and probe concentrations. No differences in the Ct-values of the MRV detection greater than 1.43 from the mean value detectable.

| Primer MRV 0.6 μM/Probe 0.2 μM | | | Primer ApTV 0.6 μM/Probe 0.1 μM | | |
|---|---|---|---|---|---|
| Primer AV (μM) | Probe AV (μM) | Ct-values MRV (6-FAM) | Primer MRV (μM) | Probe MRV (μM) | Ct-values MRV (6-FAM) |
| 0.5 | 0.08 | 28.26 | 0.5 | 0.18 | 28.70 |
| 0.5 | 0.08 | 27.84 | 0.5 | 0.18 | 29.45 |
| 0.6 | 0.08 | 29.03 | 0.6 | 0.18 | 27.10 |
| 0.6 | 0.08 | 33.79* | 0.6 | 0.18 | 29.04 |
| 0.7 | 0.08 | 27.96 | 0.7 | 0.18 | 27.90 |
| 0.7 | 0.08 | 27.83 | 0.7 | 0.18 | 28.64 |
| 0.5 | 0.12 | 28.00 | 0.5 | 0.22 | 29.40 |
| 0.5 | 0.12 | 28.66 | 0.5 | 0.22 | 28.84 |
| 0.6 | 0.12 | 27.25 | 0.6 | 0.22 | 29.53 |
| 0.6 | 0.12 | 27.37 | 0.6 | 0.22 | 28.82 |
| 0.7 | 0.12 | 28.00 | 0.7 | 0.22 | 28.87 |
| 0.7 | 0.12 | 27.38 | 0.7 | 0.22 | 28.62 |
| Average |  | 27.96 | Average |  | 28.74 |
| Standard deviation |  | 0.54 | Standard deviation |  | 0.68 |
| Max Ct-value |  | 29.03 | Max Ct-value |  | 29.53 |
| (difference) |  | (+1.07) | (difference) |  | (+0.79) |
| Min Ct-value |  | 27.25 | Min Ct-value |  | 27.10 |
| (difference) |  | (−0.71) | (difference) |  | (−1.43) |

To show the robustness of the method, three different operators, three days, three batches of each primer and probe, three extraction kits and PCR kits were tested with two MagNA Pure LC extractors and two LightCycler 480 PCR machines. The mean Ct-value of the MRV detection (8 single determinations per sample) was investigated to show the robust detection of the virus.

MRV could be detected in the 24 determinations (mean of 8 replicates) in the investigation of different reagent lots, with a standard deviation of 1.00 Ct-value (table 6). In three cases, one or two of the eight replicates per sample failed. However, overall the samples are termed positive.

TABLE 6

Results of the investigation of different reagent lots. In all 24 determinations the MRV could be detected. Additionally, the determined Ct-values showed a standard deviation of 1.00 Ct-value.

| Assay | PCR/ extraction kit lot no. | Primer and probe lot | | | | Ct-value MRV (6-FAM) | Average | StDev |
|---|---|---|---|---|---|---|---|---|
|  |  | AV primer | AV probe | MRV primer | MRV probe |  |  |  |
| 09110DW 24 Feb. 2009 | 10710420/ 14288500 | 1 | 1 | 1 | 1 | 28.33 | 28.95 | 1.00 |
|  |  | 2 | 2 | 1 | 1 | 31.34* |  |  |
|  |  | 1 | 2 | 2 | 1 | 28.21 |  |  |

TABLE 6-continued

Results of the investigation of different reagent lots. In all 24 determinations the MRV could be detected. Additionally, the determined Ct-values showed a standard deviation of 1.00 Ct-value.

| Assay | PCR/ extraction kit lot no. | Primer and probe lot | | | | Ct-value MRV (6-FAM) | Average | StDev |
|---|---|---|---|---|---|---|---|---|
| | | AV primer | AV probe | MRV primer | MRV probe | | | |
| | | 1 | 1 | 3 | 2 | 30.34 | | |
| | | 2 | 2 | 2 | 2 | 27.81 | | |
| | | 2 | 2 | 2 | 2 | 28.08 | | |
| | | 3 | 2 | 2 | 3 | 28.88 | | |
| | | 3 | 3 | 3 | 3 | 28.97 | | |
| 09112SG 25 Feb. 2009 | 13633721/ 14237900 | 1 | 1 | 1 | 1 | 28.66 | | |
| | | 2 | 2 | 1 | 1 | 27.70 | | |
| | | 1 | 2 | 2 | 1 | 30.96 | | |
| | | 1 | 1 | 3 | 2 | 28.78 | | |
| | | 2 | 2 | 2 | 2 | 29.15* | | |
| | | 2 | 2 | 2 | 2 | 26.96** | | |
| | | 3 | 2 | 2 | 3 | 27.96 | | |
| | | 3 | 3 | 3 | 3 | 28.89 | | |
| 09122GS 02 Mar. 2009 | 14532820/ 13632100 | 1 | 1 | 1 | 1 | 28.85 | | |
| | | 2 | 2 | 1 | 1 | 29.34 | | |
| | | 1 | 2 | 2 | 1 | 29.91 | | |
| | | 1 | 1 | 3 | 2 | 29.22 | | |
| | | 2 | 2 | 2 | 2 | 28.90 | | |
| | | 2 | 2 | 2 | 2 | 28.90 | | |
| | | 3 | 2 | 2 | 3 | 29.07 | | |
| | | 3 | 3 | 3 | 3 | 29.68 | | |

*Only 7 of 8 values positive
**Only 6 of 8 values positive

Internal Positive Control for Nucleic Acid Extraction

To control the efficiency of every extraction the ApTV extraction-internal positive control (EX-IPC) was spiked into every sample. The nucleic acids of the EX-IPC and MRV were amplified and detected by a different primer and probe set in a one step RT-PCR. Therefore, a competitive inhibition of one of the two targets is possible, when the concentration of one of the two targets is too high. Therefore, the concentration of the EX-IPC has to be adjusted to a concentration, that guaranteed the robust detection of the EX-IPC and also a sensitively detection of MRV.

To show the robustness of the EX-IPC, 100, 200 and 300 pg/ml of the ApTV were used, with MRV concentrations of $10^2$ and $10^3$ $TCID_{50}$/ml. Additionally, one sample without MRV was used. Per MRV and ApTV concentration, one determination was performed, in total nine determinations (six with MRV and three without MRV). The influence on the EX-IPC determination within MRV-free B1 samples (NGK-EX-IPC) was investigated.

Only slightly differences in the MRV determination were observed with a maximal standard deviation of 0.56 Ct-values with EX-IPC concentrations in the range of 100-300 pg/mL. The EX-IPC determination in samples without MRV (NGK-EX-IPC) had an equal low standard deviation (0.46 Ct-values; table 7). The evaluation of 25 NGK-EX-IPC controls showed a mean Ct-value of 28.39 (Standard Deviation 1.37).

TABLE 7

Ct-values of the MRV determinations with different EX-IPC concentrations.

| Conc. of the EX-IPC | Ct-values at different MRV concentrations (TCID50/mL) | | |
|---|---|---|---|
| | $10^3$ (6-FAM) | $10^2$ (6-FAM) | NGK-EX-IPC (Cy5) |
| 300 pg/ml | 26.74 | 29.03 | 26.66 |
| 200 pg/ml | 26.24 | 29.17 | 27.12 |
| 100 pg/ml | 26.20 | 30.06 | 27.57 |
| Average | 26.39 | 29.42 | 27.12 |
| StDev | 0.30 | 0.56 | 0.46 |

Other Controls

The second control (MRV-PC) controls the function of the 6-FAM labeled probe for the detection of MRV. The MRV-1 strain will be used at a concentration of 102 TCID50/mL in a MRV free B1 sample.

The MRV-PC will be used for every assay. No ApTV will be spiked into the MRV-PC sample. The Ct-values for the MRV-PC will be monitored in a control chart to see slightly differences during time for the performance of the assay. The MRVPC will be spiked into a MRV-free B1 sample (NGK). The control is called NGK-MRV-PC.

The third RTD-PCR control (MRV-IPC) is necessary to check the accurate performance of the amplification and detection during the RTD-PCR. The MRV-IPC is a 256 base pairs long ssRNA construct. The construct was produced by the company Panomics (Fremont, Calif.). The fragment was synthesized and cloned into the KpnI and SacI sites of a T3/T7 transcription vector (pGA4-ampR). It was prepared as final ssRNA solutions of 10 ng/mL of ssRNA. To prevent a non-specific absorption of the low concentration of ssRNA to the tube, 100 ng/μL yeast tRNA in 1×TE (pH 8.0) were added. The MRV-IPC will be amplified and detected by the ApTV specific primers and probe. The control demonstrates the functionality of the RTD-PCR in every assay. This control can distinguish between extraction and PCR errors.

The forth control is the NTC (no template control). Here, only PCR water is used as template in the RTD-PCR. This control is a negative control for the assay and is used to show any contaminations during the performance of the assay.

Detection of MRV and EX-IPC

To show that there are no false positive results resulting from cross contamination during the nucleic acid extraction, $10^5$ $TCID_{50}$/ml MRV samples and MRV free samples were extracted crosswise. Only the samples spiked with MRV should show a positive detection of MRV.

MRV was detected in all samples where MRV was added. All samples without MRV were analysed as negative for MRV. The EX-IPC was detected in each case.

CONCLUSIONS

The evaluation of the EX-IPC showed a robust performance. The investigation of slightly differences in primer and probe concentrations showed no significant influence. Additionally, the use of different batches of reagents showed also no influence on the RTD-PCR performance.

There were no false positive or false negative results, and no cross contamination during the nucleic acid extraction between samples spiked with $10^5$ $TCID_{50}$/ml and samples without a MRV was observed.

It will be understood that the invention has been described by way of example only and modifications may be made whilst remaining within the scope and spirit of the invention.

The invention claimed is:

1. A method for verifying the reliability of an assay to detect a first virus comprising the steps of:
   (a) adding an exogenous second virus to a biological sample prior to analysing the viral nucleic acids or polypeptides from the biological sample; and
   (b) analysing the viral nucleic acids or polypeptides from the biological sample to detect the first and second virus; wherein the first and second virus are the same type of virus and the second virus is an internal positive control; and wherein the first virus is an animal virus and the second virus is a plant virus.

2. A method of confirming that a biological sample is substantially free from a first virus, comprising the steps of:
   (a) adding an exogenous second virus to a biological sample prior to analysing the nucleic acids from the biological sample;
   (b) analysing the nucleic acids from the biological sample to detect the first and second virus; and
wherein the first and second virus are the same type of virus and the second virus is an internal positive control; and wherein the first virus is an animal virus and the second virus is a plant virus.

3. The method of claim 1, wherein the first and second viruses are both filamentous viruses, icosahedral viruses, or complex viruses.

4. The method of claim 1, wherein the second virus is *Alliaria petiolata* Tymovirus (ApTV) comprising genomic RNA comprising RNA comprising a poly-ribonucleic acid sequence according to SEQ ID NO: 1-4, where thymidine bases are substituted with uridine bases.

5. The method of claim 1, wherein the first virus is an icosahedral animal virus.

6. The method of claim 1 wherein the biological sample is selected from the group consisting of a vaccine; an intermediate in vaccine production; blood; blood products, serum, plasma, red blood cells, white blood cells, platelets; tissue samples, bone marrow, kidney, liver, heart, lung, and skin.

7. The method of claim 2, wherein the biological sample is an influenza vaccine or an intermediate in the production of an influenza vaccine.

8. The method of claim 7, wherein the influenza vaccine is produced in cell-culture.

9. The method of claim 2 further comprising detecting the presence of the first virus in the absence of detecting the second virus.

10. The method of claim 2 further comprising detecting the presence of the second virus in the absence of the first virus.

11. The method of claim 9 further comprising the step of extracting the nucleic acids from the biological sample after adding the exogenous second virus to the biological sample.

* * * * *